(12) United States Patent
Levin

(10) Patent No.: US 11,266,800 B2
(45) Date of Patent: Mar. 8, 2022

(54) NASAL DELIVERY DEVICE AND METHODS OF USE

(71) Applicant: Bruce H. Levin, Oceanside, NY (US)

(72) Inventor: Bruce H. Levin, Oceanside, NY (US)

(\*) Notice: Subject to any disclaimer, the term of this patent is extended or adjusted under 35 U.S.C. 154(b) by 514 days.

(21) Appl. No.: 16/186,396

(22) Filed: Nov. 9, 2018

(65) Prior Publication Data

US 2019/0143054 A1 May 16, 2019

Related U.S. Application Data

(62) Division of application No. 14/637,066, filed on Mar. 3, 2015, now abandoned.

(60) Provisional application No. 62/102,958, filed on Jan. 13, 2015.

(51) Int. Cl.
*A61M 15/08* (2006.01)
*A61M 15/00* (2006.01)
*A61M 11/00* (2006.01)

(52) U.S. Cl.
CPC ........ *A61M 15/08* (2013.01); *A61M 15/0003* (2014.02); *A61M 11/007* (2014.02); *A61M 15/0041* (2014.02); *A61M 2206/16* (2013.01)

(58) Field of Classification Search
CPC .. A61M 11/00; A61M 15/0003; A61M 15/08; A61M 15/0041; A61M 2206/16; A61M 11/0007; B65D 83/20; B05B 11/047
See application file for complete search history.

(56) References Cited

U.S. PATENT DOCUMENTS

| | | | | |
|---|---|---|---|---|
| 5,664,557 A | * | 9/1997 | Makiej, Jr. ............ | A61M 15/00 128/200.23 |
| 6,715,485 B1 | * | 4/2004 | Djupesland ....... | A61M 16/0866 128/203.15 |
| 2010/0282246 A1 | * | 11/2010 | Djupesland ....... | A61M 15/0098 128/200.14 |
| 2011/0282268 A1 | * | 11/2011 | Baker .................. | A61M 15/08 604/20 |
| 2013/0158475 A1 | * | 6/2013 | Xia ...................... | A61M 11/06 604/94.01 |

\* cited by examiner

*Primary Examiner* — Margaret M Luarca
(74) *Attorney, Agent, or Firm* — Keith A. Vogt; Keith Vogt, Ltd

(57) ABSTRACT

The present invention provides a drug delivery system that includes a housing configured to contain one or more dispensers. Each dispenser includes an activation mechanism, a nozzle configured to direct the medicament to a predetermined area in the nasal passageway. The nozzles may be configured to create a spray pattern that is about 50-degrees to direct the delivery of a medicament to the sphenopalatine ganglion.

5 Claims, 6 Drawing Sheets

Tandem dispensers: one for each nares. Each is pre-loaded with a pre-determined dosage. A single press of the button activates a spring-loaded piston which, in, turn, delivers the desired dosage through the spray end.

The shape of the spray end is such that the device will target the SPG (at the rear of the nasal passage).

NASAL DELIVERY DEVICE AND METHODS OF USE

RELATED APPLICATIONS

This application is a divisional of U.S. Ser. No. 14/637,099 filed on Mar. 3, 2015, which claims the benefit U.S. Provisional Application No. 62/102,958, filed Jan. 13, 2015 both of which are herein incorporated by reference.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

The present invention relates to a nasal delivery device for the intranasal delivery of a medicament. Delivery of a medicament through the nasal passageway is often the optimal mode of delivery for certain medicaments. To accomplish this, using rudimentary devices and methods, a syringe or cotton swab is used.

In syringe or plunger-type devices, a user exerts pressure on a plunger to urge the liquid out of the sprayer. However, to properly administer the medicament through a nasal passageway, the spray nozzle must generate a spray. A therapeutically effective spray is not achieved unless the plunger is actuated at a certain speed that is sufficient to create a spray. A failure to generate sufficient speed results in the liquid being ejected in a stream or drops instead of a spray. Too much speed may result in overdosing. Thus, traditional methods of nasal delivery, while affording a measure of simplicity for the user, have a number of problems, including waste and cost arising from errors in drug administration; and over or under dosing arising from inexact administration of the drug. Moreover, the easier a therapeutic drug is to administer, the more interested a patient will be in the drug. This may then result in an increase in compliance with taking the drug and a resulting increase in use.

BRIEF SUMMARY OF THE INVENTION

In one embodiment, the present invention relates to a medical device for intranasal delivery of a medicament. The medicament may be any type of medicament suitable for nasal administration and delivery in the form of a spray.

In other embodiments, the present invention ensures that a complete dosage of the medicament is delivered, especially to specific areas in the nasal cavity such as the rear of the nasal cavity where the sphenopalatine ganglion (hereinafter, the "SPG") is located.

According to an embodiment of the invention, the nasal spray device includes a body having a container for holding a medicament to be administered, and an actuator that is actuatable to cause the delivery of the medicament out of the container. More specifically, the present invention relates to a delivery device for delivery of a medicament to a user including a container defining a reservoir for storing the medicament, a body in which the container is received, a spray nozzle arranged on one end of the body and the container for receiving medicament expelled from the container, and an actuator.

In further embodiments, the present invention includes a nozzle configured to target a specific location in the nasal cavity. A preferred targeted location is the SPG, which is relatively inaccessible as a result of being located below a region of epithelium in the posterior portion of the nasal cavity, inferior to and including the spheno-ethmoidal recess.

In yet other embodiments, the present invention is directed to delivery systems that administer single doses of one or more substances, for example a liquid, powder, or gel, to each nostril of a user. As used herein, the term "delivery system" is interchangeable with "delivery device" or "device." The delivery systems of the present invention may deploy a pressurized container to hold and deliver a predetermined volume of substance to a particular destination with the administration, independent of the coordination of the user.

In certain embodiments, the delivery systems disclosed herein offer one or more of the following advantages: cost savings (reduces waste from reducing errors in administration); improved efficacy from the administration of consistent, premeasured dosages; convenience and ease of use; improved patient compliance; improved safety; improved performance due to the use of a nozzle configured to direct the delivery of the medicament to a target location such as the SPG.

In still further embodiments, the disclosed drug delivery systems include a housing; a button on a surface of the housing that actuates a firing mechanism comprising a piston or plunger in contact with the button through a link; actuation of the button releases the piston which drives the medicament through the nozzle in the form of a single dosage or unit spray.

In other embodiments, the disclosed drug delivery system includes tandem dispensers for the delivery of a unit dose of medicament to each nostril. The dosage forms can also be included in a cartridge that is replaceable in a drug delivery system. The housing is configured in such embodiments to accept a cartridge containing one or more dosage forms, which may be contained in blister form.

Other embodiments include delivery systems that may include a button, paddle, lever or rocker that is flush with the surface of the delivery system in a storage mode and can be raised or tilted up on one end thereof into the ready position to indicate that the device is ready for use.

In additional embodiments, the dispensing mechanism uses the button, paddle, rocker or charging lever to store energy in a spring. When the charging button, paddle, rocker or charging lever is pressed, the travel compresses a spring that is locked by the dispensing release. This spring is then released or triggered by a dispensing release button to fire the piston or ram to dispense the fluid.

Other embodiments use pressurized dispensing. This may be predetermined to promote accurate unit dosing.

In some embodiments, the present invention provides intranasal delivery systems that are able to dispense single or controlled, premeasured doses of one or more substances. In other embodiments, the system is configured to dispense single or controlled, premeasured doses of one or more substances to each nostril.

Other embodiments of the delivery systems of the present invention incorporate ergonomic designs that promote ease of operation and that reduce the time needed for administering the predetermined substances. Other designs include using predetermined nozzle lengths configured to conform to differing anatomical configurations.

As used herein, the term "substance" includes but is not limited to one or more active-ingredient-containing substances wherein the active ingredient may be biologic agents such as a protein, peptide, vaccine, or an active pharmaceutical ingredient ("API"), for example a pharmaceutical drug such as a prescription drug, generic drug, or over-the-counter pharmaceutical, neutraceutical or homeopathic product. The substance may be in an aqueous, gel, powder, solution, emulsion, crystals or suspension form. As used herein, the term "substance" is interchangeable with the terms "drug," "drug product," "medication," "liquid," "biologic," "active ingredient" or "API." As used herein, an "active ingredient" or API is any component intended to furnish pharmacological activity or other direct effect in the diagnosis, cure, mitigation, treatment, or prevention of disease, or to affect the structure or any function of the body of humans or other animals. As used herein, the term "unit dosage form" is interchangeable with the terms "bottle," "vial," "unit-dose," "dosage form," "unit-dose vial," "blister," "dosage blister," "ampule" or "container."

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

As shown in FIGS. 1-6, intranasal delivery device 100 may include tandem dispensers 110 and 112 which are combined as a housing configured to contain unit dosage forms as disclosed herein which may be in the form of single unit dose as well as sterile containers used to hold and dispense a wide range of substances. In specific preferred embodiments, the delivery systems of the present invention may also be designed to administer intranasal drugs, including but are not limited to drug products, chemical drugs, or biologics for migraines, pain management, hormones, sleep dysfunction, erectile dysfunction, central nervous system disorders, seizures, emesis or allergies.

Figure 1:
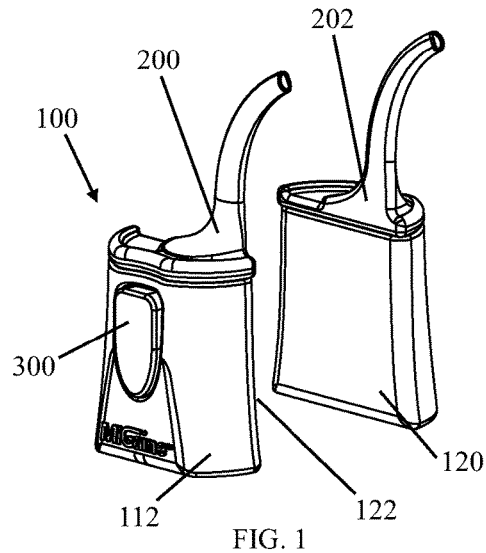
FIG. 1 is an exploded, perspective view of an embodiment of the present invention.
Figure 2:
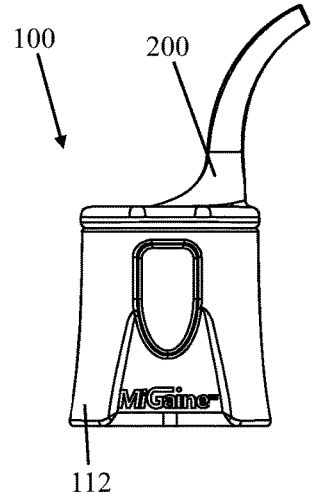
FIG. 2 is a right side view of an embodiment of the present invention.
Figure 3:
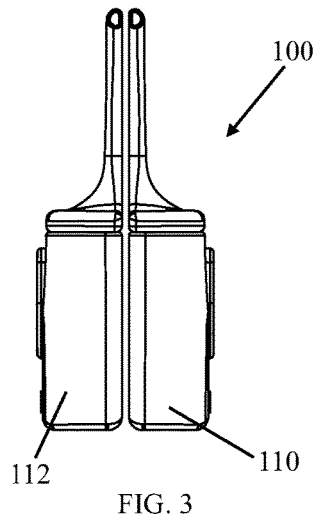
FIG. 3 is a front view of an embodiment of the present invention.
Figure 4:
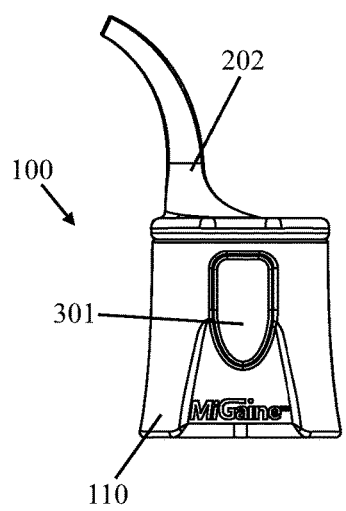
FIG. 4 is a left side view of an embodiment of the present invention.
Figure 5:
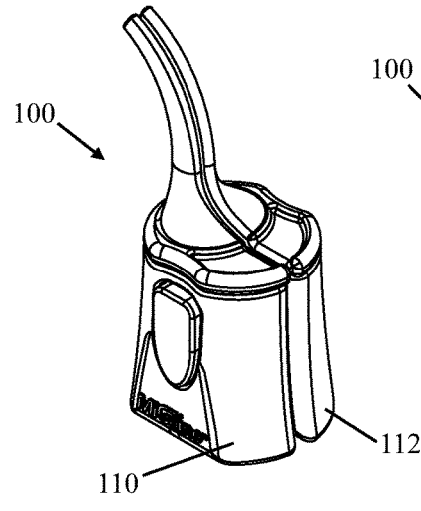
FIG. 5 is another perspective view of an embodiment of the present invention.
Figure 6:
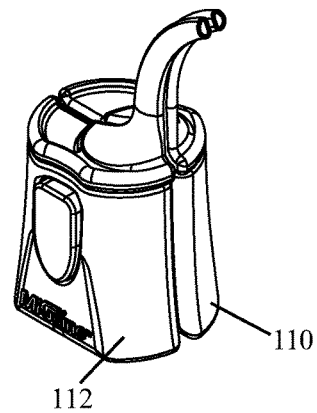
FIG. 6 is yet another perspective view of an embodiment of the present invention.

Each tandem dispenser 110 and 112 includes a planar surface 120 and 122 configured to mate together as shown in FIG. 3. In addition, the dispensers are complimentary mirror images that join together to form the appearance of a single unit. In addition, the dispensers may be configured to be releasably joined together to promote ease of handling prior to use.

Figure 7:
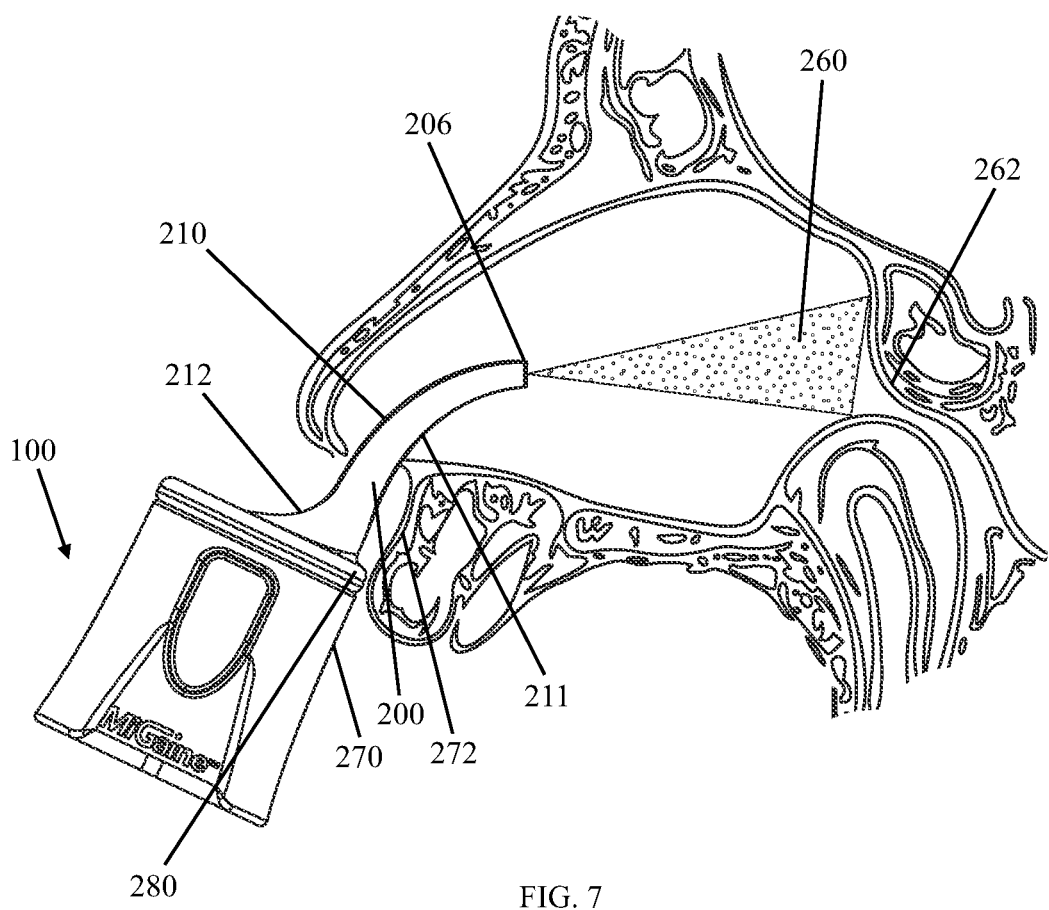
FIG. 7 illustrates the operation of an embodiment of the present invention.

To deliver the medicament to an intended area, each dispenser includes a nozzle 200. As shown in FIG. 7, in a preferred embodiment, each nozzle includes curved portions 210-212 that are configured to deliver a spray 260 through port 206 to a designated area 262 which may be an area that enables a medicament to reach the SPG.

In addition, the overall length and dimensions of the nozzle may be arranged in differing sets of configurations. Rather than a one size fits all design, the differing configurations may be provided so as to provide a configuration that has been customized for a particular anatomical configuration. In this way, the effectiveness of the device is enhanced.

Certain embodiments of personal delivery systems described herein include actuators 300 and 301 may be buttons, lever or other firing mechanisms on the top surface of the delivery system to actuate the dispensing of the substance. In one embodiment, the button is raised above the surface to indicate that it is ready for use, In other embodiment, the button may lie flat against the top of the delivery system in a storage position and one end of the button may be tilted upward, away from the device surface in the ready position. In the ready position, depressing the button causes a piston in communication with a spring (not shown) to compress the dosage form and dispense the substance contained therein.

In another embodiment, the present invention provides a delivery system described herein that includes a compressed air or fluid reservoir, which is used to drive a plunger into the dosage form. This embodiment can include a regulator to ensure consistent operation as the reservoir pressure is reduced. A compressed air or fluid reservoir allows for a lower activation force for the operator.

Other embodiments of the delivery system described herein may include the medicament in a dosage form that is a compressed aerosol that is released when actuated.

Certain embodiments of the delivery system described herein include a compressed spring, which is used to drive a plunger into the dosage form. In this embodiment the spring, which is compressed prior to use, provides a more consistent delivery since operator input is limited triggering the release of stored energy rather than providing the force to drive the plunger into the dosage form.

In yet other aspects, the present invention provides a dispensing unit including a dosage form that includes one or more internal chambers, which contains a substance to be administered, which is in fluid communication with, or is adjacent to, a pierceable section of wall of the unit dosage form. This wall may be an interior or exterior wall. In certain embodiments, a piercer may move toward and pierce the pierceable section of the chamber to allow dispersion of the substance, or the pierceable section may move toward and be pierced by the piercer.

In use, tandem dispensers 110 and 112 typically contain a unit dose of a medicament to be used in each of the nares. The length of nozzle 200 is dimensioned to locate port 206 to direct predetermined spray pattern 260 to a specific region in the nasal passage. For the embodiment shown in FIG. 7, the targeted area is the SPG 262 and medicament is an anesthetic for the treatment of a migraine. By coordinating the dimensions of the nozzle with a predetermined spray pattern of expelled medicament, a targeted and concentrated treatment may be delivered.

To assist a user in the placement of a dispenser, nozzle 200 and edge 270 form a line that may be positioned along a user's upper lip 272. This acts as a guide. Edge 270 and curved portion 212 create shoulders that prevent further insertion of the device. This, too, may be dimensioned to coordinate the accurate placement of the device. In one application, the device is inserted until shoulders 212 and 280 engage a user and indicate the device is in an optimal placement.

Figure 8:
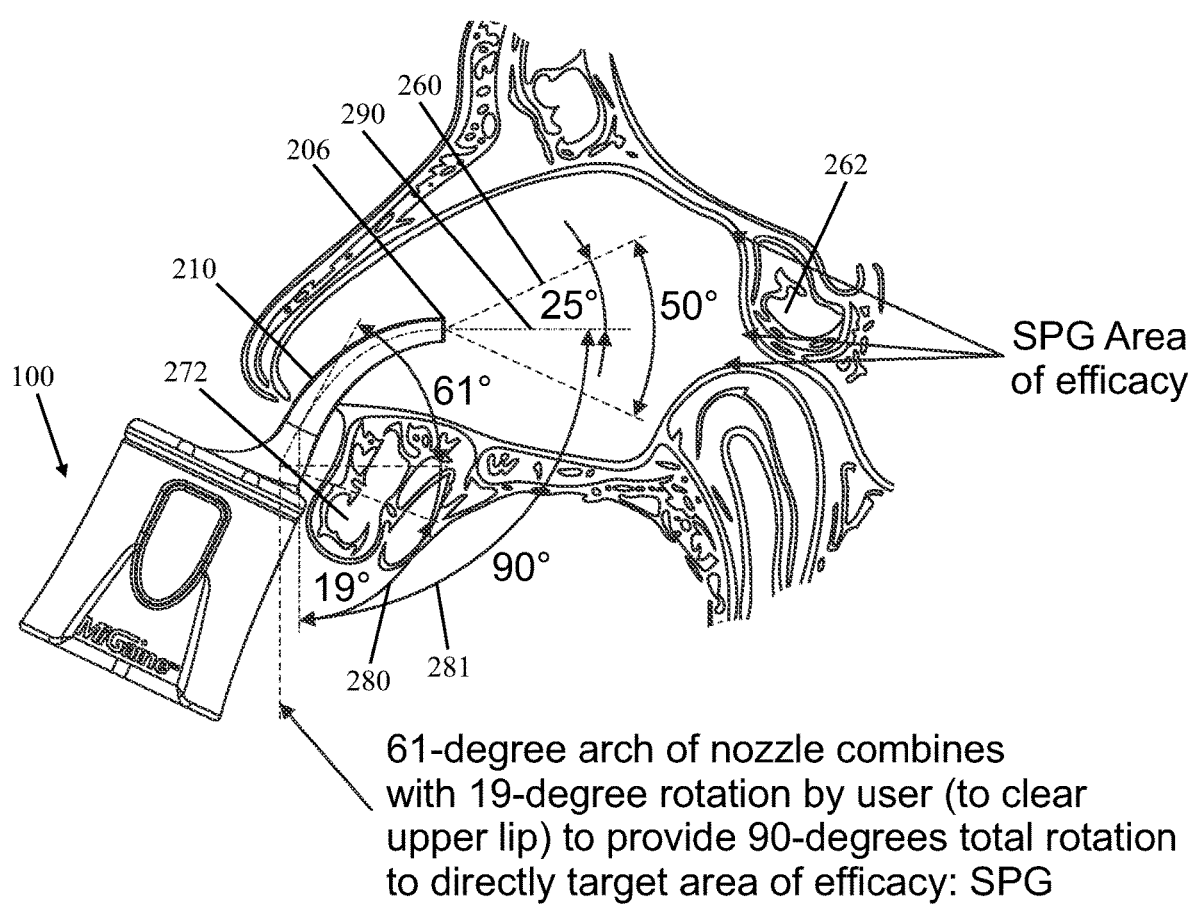
FIG. 8 illustrates another preferred embodiment of the present invention and the associated mode of operation.

FIG. 8 illustrates another preferred embodiment of the present invention that is adapted to provide optimal targeting of SPG 262 by spray pattern 260. As shown, it has been determined that configuring nozzle 206 to create a spray pattern 260 that is about 50-degrees provides optimal delivery of a medicament to SPG 262.

It has also been found that to improve delivery, curved portion 210 may be configured to form an arch of about 61-degrees. When this arch is combined with an approximate 19-degree rotation as shown by line 280 by a user to clear upper lip 272, the device provides approximately 90-degrees of total rotation from its original vertical position as shown by line 281 to directly target SPG 262. Configuring the device in this manner centers spray 260 on line 290 to concentrate the medicament on the desired area such as SPG 262.

Figure 9:
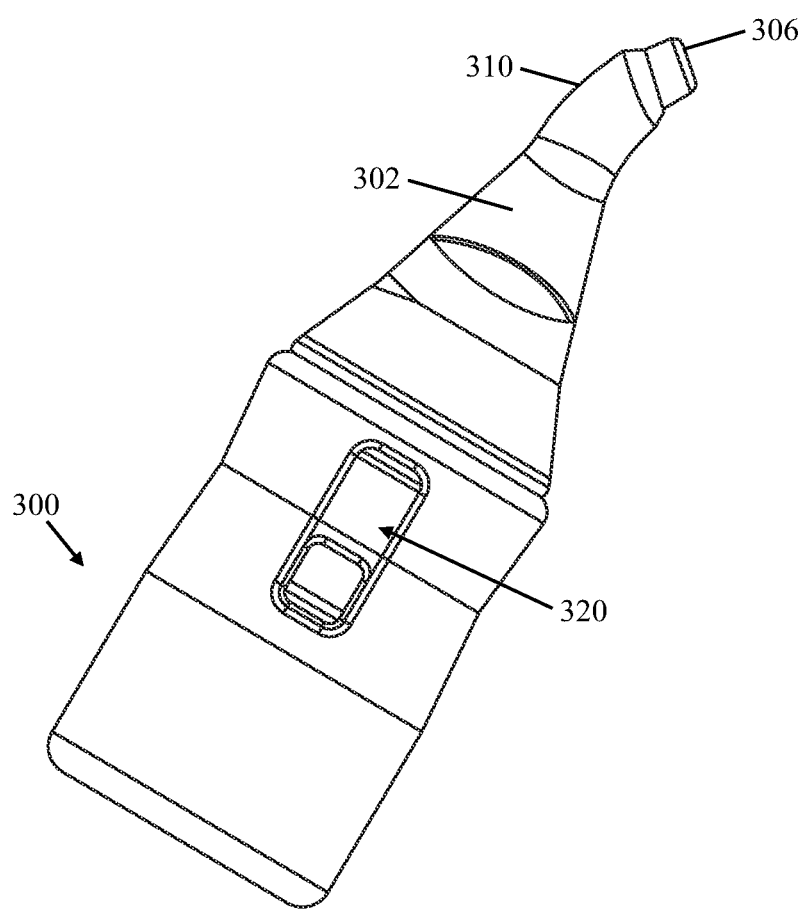
FIG. 9 is perspective view of an alternate embodiment of the present invention.

FIG. 9 shows yet another embodiment of the present invention providing a container 300 that may be configured to provide a single dosage of medicament. The device includes a nozzle 302 having a curved portion 310, which is adapted to deliver a spray through port 306 to a designated area such as SPG 262. In addition, nozzle 302 may be conical or tapered in shape so that upon insertion into the nasal cavity, a seal is formed such that when the device is activated, no spray escapes through the nasal cavity. Actuator 320 is positioned such that when a user grasps the device, the user's thumb may be used to actuate the device. To do this, actuator 320 is located perpendicular to the user's nasal passageway.

Figure 10:
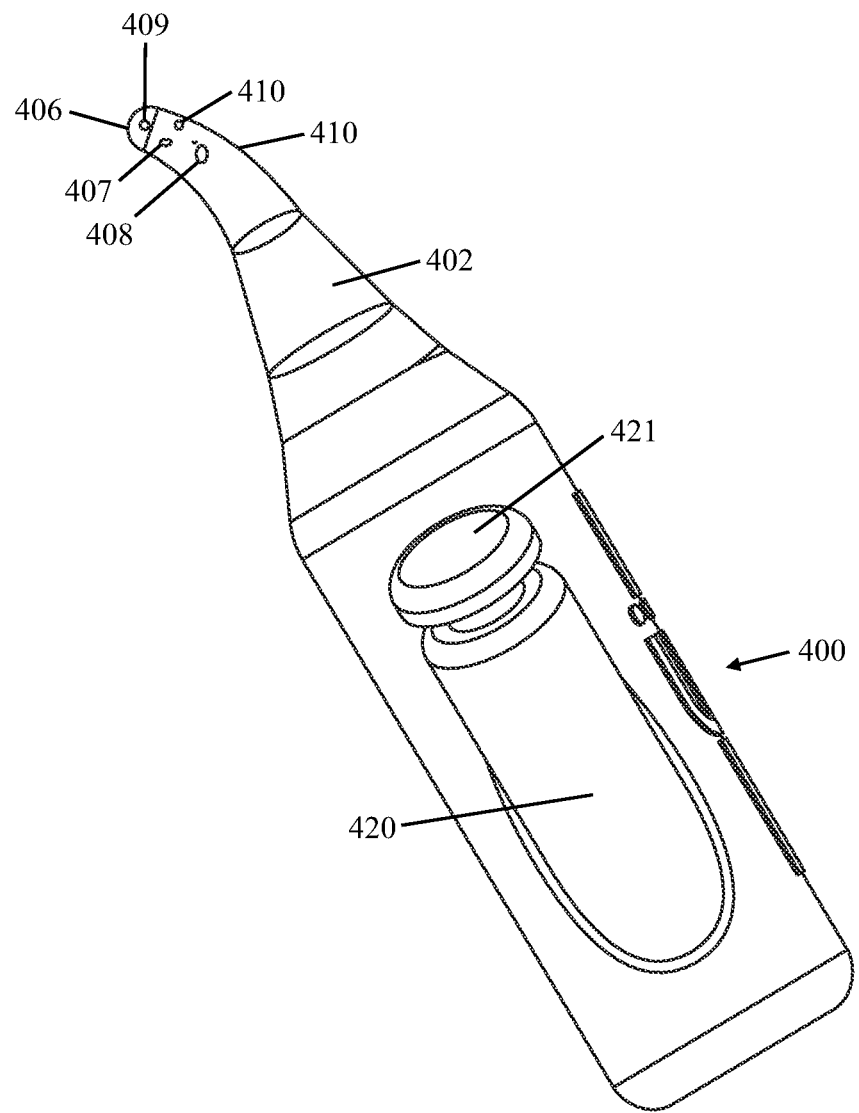
FIG. 10 is perspective view of another embodiment of the present invention.

FIG. 10 shows yet another embodiment of the present invention providing a container 400 that may be configured to provide a single dosage of medicament. The device includes a nozzle 402 having a curved portion 410, which is adapted to deliver a spray through port 406 to a designated area such as SPG 262. In addition, nozzle 402 may be conical or tapered in shape so that upon insertion into the nasal cavity, a seal is formed such that when the device is activated, no spray escapes through the nasal cavity. Actuator 420 is positioned such that when a user grasps the device, the user's thumb may be used to actuate the device. To do this, actuator 420 is located perpendicular to the user's nasal passageway with button 421 positioned to point at the user.

In other embodiments, as shown in FIG. 10, the device may be used as an intranasal cleaner in addition to delivering a medicament. The other described dispensers may be used in a similar manner. To reach other desired areas in the nasal cavity, other openings 407-410 may be used. Either a single opening may be provided to direct the delivery of a fluid or medicament to another predetermined area of the nasal cavity, or multiple openings may be used. In other embodiments, the sizes and the configurations of the openings may be varied as desired. Lastly, the nozzle configurations described may also be used with the other disclosed embodiments.

Figure 11:
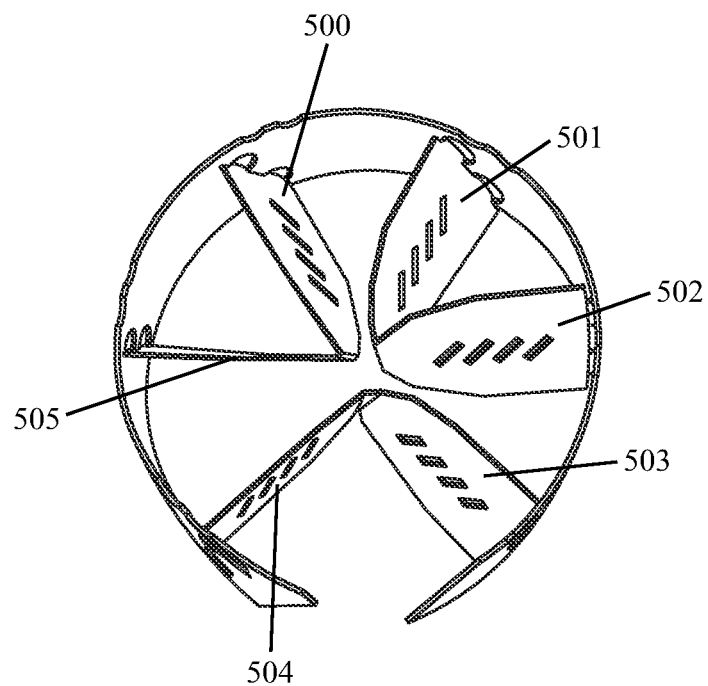
FIG. 11 shows an alternate embodiment of a nozzle that may be used in the present invention.
Figure 12:
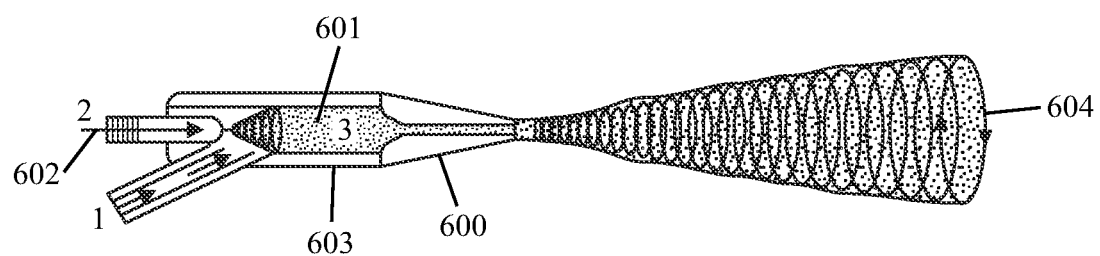
FIG. 12 shows yet another embodiment of a nozzle that may be used in the present invention.

In other embodiments, the nozzles of the various disclosed embodiments may be configured to create a vortex of fluid, powder, or combination thereof. Creating a vortex permits a fluid, air or spray to entraining medicaments or other desired substances. The vortex also creates a precise flow that may be targeted with more precision to a desired location. As shown in FIG. 11, one possible way to create a vortex is to include fins 500-505 inside a nozzle. As shown in FIG. 12, nozzle 600 of an alternate embodiment may include a mixing chamber 601 feed by inlets 602 and 603 to a create vortex that has circular, rotating pattern 604 that may be directed to an area or anatomical location of interest.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A method for delivering a medication to the sphenopalatine ganglion, which comprises:
   providing a housing having releasably connected first and second dispensers, each of said dispensers including a nozzle disposed between a pair of shoulders and said nozzle configured to form an arch of about 61-degrees;
   disconnecting said dispensers from each other and using each respective dispenser to deliver a unit dosage by inserting a nozzle until said shoulders prevent further insertion;
   rotating said dispenser approximately 19 degrees to direct the medication to the sphenopalatine ganglion.

2. The method of claim 1 wherein each of said nozzles are configured to create a spray pattern that is about 50-degrees to direct the delivery of a medicament to the sphenopalatine ganglion.

3. The method of claim 1 wherein each of said nozzles are conical in shape so that upon insertion, a seal is formed such that when the device is activated spray is contained in the nasal cavity.

4. The method of claim 1 wherein said dispensers include an activation mechanism that is positioned such that when a user grasps a dispenser, the user's thumb may be used to actuate the device.

5. The method of claim 1 wherein said nozzles generate a vortex of fluid.

* * * * *